US007235295B2

(12) United States Patent
Laurencin et al.

(10) Patent No.: US 7,235,295 B2
(45) Date of Patent: Jun. 26, 2007

(54) POLYMERIC NANOFIBERS FOR TISSUE ENGINEERING AND DRUG DELIVERY

(76) Inventors: Cato T. Laurencin, 580 Milford Rd., Earlysville, VA (US) 22936; Lakshmi Sreedharan Nair, 264 Colonnade Dr. #22, Charlottesville, VA (US) 22903; Subhabrata Bhattacharyya, 162-4 Hessian Hills Way, Charlottesville, VA (US) 22901; Harry R. Allcock, 434 Kemmerer Rd., State College, PA (US) 16801; Jared D. Bender, 297 Easterly Pkwy., State College, PA (US) 16801; Paul W. Brown, 352 E. Irvin Ave., State College, PA (US) 16801; Yaser E. Greish, 879 Southgate Dr. #105, State College, PA (US) 16801

( * ) Notice: Subject to any disclaimer, the term of this patent is extended or adjusted under 35 U.S.C. 154(b) by 0 days.

(21) Appl. No.: 10/938,493

(22) Filed: Sep. 10, 2004

(65) Prior Publication Data
US 2005/0112349 A1 May 26, 2005

Related U.S. Application Data

(60) Provisional application No. 60/501,897, filed on Sep. 10, 2003.

(51) Int. Cl.
*D02G 3/00* (2006.01)
*A61F 2/02* (2006.01)
*A61B 17/06* (2006.01)
*B29C 70/08* (2006.01)

(52) U.S. Cl. ............... 428/364; 623/23.74; 623/11.11; 606/222; 428/36.3

(58) Field of Classification Search ............. 623/11.11, 623/23.74; 428/364, 36.3; 606/139, 222
See application file for complete search history.

(56) References Cited

U.S. PATENT DOCUMENTS

| 1,975,504 | A |   | 10/1934 | Formhals |         |
|-----------|---|---|---------|----------|---------|
| 2,160,962 | A |   | 6/1939  | Formhals |         |
| 2,187,306 | A |   | 1/1940  | Formhals |         |
| 5,053,451 | A | * | 10/1991 | Allcock et al. | 524/600 |
| 5,629,009 | A | * | 5/1997  | Laurencin et al. | 424/426 |
| 5,766,618 | A | * | 6/1998  | Laurencin et al. | 424/426 |
| 6,077,916 | A | * | 6/2000  | Laurencin et al. | 525/419 |
| 6,093,758 | A | * | 7/2000  | Allcock et al. | 524/116 |
| 6,392,008 | B1 | * | 5/2002 | Allcock et al. | 528/399 |
| 6,605,237 | B2 | * | 8/2003 | Allcock et al. | 252/500 |
| 6,685,956 | B2 | * | 2/2004 | Chu et al. | 424/423 |
| 6,689,166 | B2 | * | 2/2004 | Laurencin et al. | 623/11.11 |
| 6,737,447 | B1 | * | 5/2004 | Smith et al. | 523/105 |
| 2002/0173213 | A1 |   | 11/2002 | Chu et al. | |
| 2003/0050711 | A1 |   | 3/2003  | Laurencin et al. | |

FOREIGN PATENT DOCUMENTS

WO   WO 01/26702    4/2001

WO   WO 0126702 A2 * 4/2001

OTHER PUBLICATIONS

Allcock, "Developments at the interface of inorganic, organic, and polymer chemistry" *Chemical and Engineering News* 63(11): 22-36 (1985).
Ambrosio, et al., "Degradable polyphosphazene/poly($\alpha$-hydroxyester) blends: degradation studies" *Biomaterials* 23: 1667-1672 (2002).
Baumgarten, "Electrostatic spinning of acrylic microfibers" *Journal of Colloid and Interface Science* 36(1): 71-79 (1971).
Bognitzki, et al., "Nanostructured fibers via electrospinning" *Advanced Materials* 13: 70-72 (2001).
Buchko, et al., "Processing and microstructural characterization of porous biocompatible protein polymer thin films" *Polymer* 40: 7397-7407 (1999).
Dayton, et al., "Use of an absorbable mesh to repair contaminated abdominal-wall defects" *Arch. Surgery* 121(8): 954-960 (1986).
Huang, et al., "Engineered collagen-PEO nanofibers and fabrics" *J Biomater Sci Polym Edn.* 12(9): 979-993 (2001).
Huang, et al., "A review on polymer nanofibers by electrospinning and their applications in nanocomposites" *Composites Science and Technology* 63: 2223-2253 (2003).
Ibim, et al., "Novel polyphosphazene/poly(lactide-co-glycolide) blends: miscibility and degradation studies" *Biomaterials* 18: 1565-1569 (1997).
Kenawy, et al., "Antimicrobial properties of modified and electrospun poly(vinyl phenol)" *Macromoleuclar Bioscience* 2: 261-266 (2002).
Klinge, et al., "Functional assessment and tissue response of short- and long-term absorbable surgical meshes" *Biomaterials* 22: 1415-1424 (2001).
Krishnappa, et al., "Electrospinning of polycarbonates and their surface characterization using the SEM and TEM" *Mat Res Soc Symp Proc* 702: U6.7.1-U 6.7.6 (2002).
Laurencin, et al., "Use of polyphosphazenes for skeletal tissue regeneration" *J. Biomed. Mater. Res.* 27: 963-973 (1993).
Laurencin, et al., "A highly porous 3-dimensional polyphosphazene polymer matrix for skeletal tissue regeneration" *J. Biomed. Mater. Res.* 30: 133-138 (1996).
Li, et al., "Electrospun nanofibrous structure: A novel scaffold for tissue engineering" *J Biomed Mater Res* 60: 613-621 (2002).
MacDiarmid, et al., "Electrostatically-generated nanofibers of electronic polymers" *Synthetic Metals*, 119: 27-30 (2001).
Megelski, et al., "Micro- and nanostructured surface morphology on electrospun polymer fibers" *Macromolecules* 35: 8456-8466 (2002).

(Continued)

Primary Examiner—N. Edwards

(57) ABSTRACT

Polymeric nanofibers have been developed which are useful in a variety of medical and other applications, such as filtration devices, medical prosthesis, scaffolds for tissue engineering, wound dressings, controlled drug delivery systems, cosmetic skin masks, and protective clothing. These can be formed of any of a variety of different polymers, either non-degradable or degradable. In a preferred embodiment demonstrated in the following examples, nanofibers are formed of biodegradable and non biodegradable polyphosphazenes, their blends with other polyphosphazenes or with organic, inorganic/organometallic polymers as well as composite nanofibers of polyphosphazenes with nanosized particles such as hydroxyapatites.

10 Claims, No Drawings

OTHER PUBLICATIONS

Reneker and Chun, "Nanometre diameter fibres of polymer, produced by electrospinning" *Nanotechnology* 7(3): 216-223 (1996).

Schreuder-Gibson, et al., "Protective textile materials based on electrospun nanofibers" *J. Adv. Mater.* 34: 44-55 (2002).

Senador et al., "Electrospinning of polymeric nanofibers: Analysis of jet formation" *Mat. Res. Soc. Symp. Proc.* 661: KK5.9.1-KK5.9.6 (2001).

Tsai, et al., "Different electrostatic methods for making electret filters" *J. Electrostatics* 54: 333-341 (2002).

Wang, et al., "Electrospun nanofibrous membranes for highly sensitive optical sensors" *Nano Letters* 2(11): 1273-1275 (2002).

Yashimoto, et al., "A biodegradable nanofiber scaffold by electrospinning and its potential for bone tissue engineering" *Biomaterials* 24: 2077-2082 (2003).

Zong, et al. "Structure and process relationship of electrospun bioabsorbable nanofiber membranes" *Polymer* 43: 4403-4412 (2002).

* cited by examiner

POLYMERIC NANOFIBERS FOR TISSUE ENGINEERING AND DRUG DELIVERY

CROSS-REFERENCE TO RELATED APPLICATIONS

This application claims priority to provisional U.S. Ser. No. 60/501,897, filed Sep. 10, 2003.

BACKGROUND OF THE INVENTION

This invention is generally in the field of medical applications of polymer fibers and particularly the use of polymeric nanofibers in tissue engineering, medical devices and drug delivery.

Polymer fibers have been used in numerous medical applications. For example, sutures are made of polymer fibers, either non-biodegradable polymers or biodegradable polymers such as poly(lactide-co-glycolide). Fibers are also woven or meshed to form wound dressings, tissue engineering matrices, gauzes and bandages, and drug delivery devices (where the drug is encapsulated within the polymers, and released by diffusion and/or degradation).

These polymeric fibers typically have diameters of 50 microns or greater, many in the range of 100 to 300 microns. They are limited by virtue of the inflexibility of the materials they are formed from. It would be desirable to vary the properties of these materials without having to modify the composition of the polymeric materials.

It is therefore an object of the present invention to provide new forms of polymeric fibers for use in medical applications, especially tissue engineering, medical devices, and drug delivery.

SUMMARY OF THE INVENTION

Polymeric nanofibers have been developed which are useful in a variety of medical and other applications, such as filtration devices, medical prosthesis, scaffolds for tissue engineering, wound dressings, controlled drug delivery systems, cosmetic skin masks, and protective clothing. These can be formed of any of a variety of different polymers, either non-degradable or degradable. In a preferred embodiment demonstrated in the following examples, nanofibers are formed of biodegradable and non biodegradable polyphosphazenes, their blends with other polyphosphazenes or with organic, inorganic/organometallic polymers as well as composite nanofibers of polyphosphazenes with nanosized particles such as hydroxyapatites.

DETAILED DESCRIPTION OF THE INVENTION

Polymeric Nanofibers

Polymeric nanofibers form an exciting new class of materials for various applications. For example, such materials can be used in filtration devices, medical prosthesis, scaffolds for tissue engineering, wound dressings, controlled drug delivery systems, cosmetic skin masks, protective clothing material for military applications, for developing nanocomposites, nanosensors, as materials to develop micro/nano electronic devices, materials for developing devices for electrostatic dissipation, materials for developing devices for electromagnetic interference shielding, materials for developing photovoltaic devices, materials for developing LCD devices, for developing ultra-light weight spacecraft materials, for developing highly efficient and functional catalysts as well as materials with improved electrical, optical and piezoelectric properties.

Polymeric nanofibers are polymer fibers having diameters typically between 10 nm and 1 micron, preferably between 100 and 1000 nm. They can be made using electrostatic spinning or electrospinning processes [U.S. Pat. No. 1,975,504, U.S. Pat. No. 2,160,962, U.S. Pat. No. 2,187,306 to Formhals, Baumgarten P K. J of Colloid and Interface Science 1971; 36:71–9; Reneker D H, Chun I. Nanotechnology 1996; 7:216–23]. Briefly, electrospinning uses an electric field to draw a polymer solution from the tip of the capillary to a collector. A high voltage DC current is applied to the polymer solution which causes a jet of the polymer solution to be drawn towards the grounded collector screen. Once ejected out of the capillary orifice, the charged polymer solution jet gets evaporated to form fibers and the fibers get collected on the collector. The size and morphology of the fibers thus obtained depends on a variety of factors such as viscosity of the solution, polymer molecular weight, nature of the polymer and other parameters regarding the electrospinning apparatus. The electrospinning process to form polymer nanofibers has been demonstrated using a variety of polymers [Huang, et al. Composites Science and Technology 2003; 63]. Electrostatic spinning is a process by which polymer fibers of nanometer to micrometer size in diameters and lengths up to several kilometers can be produced using an electrostatically driven jet of polymer solution or polymer melt. Due to their very small diameters, very high surface area and small pore size, these ultra thin solid fibers exhibit high flexibility in surface functionalities, light weight, unusual optical properties and superior mechanical properties compared to any other known form of material that exists today.

Nanofibers with wide ranges of diameters from 1–1000 nm can be obtained by varying various experimental parameters such as viscosity of the polymer solution, electric potential at the capillary tip, diameter of the capillary tip as well as the gap or distance between the tip and the collecting screen.

Polymers

Some of the non-degradable polymers investigated in the form of nanofibers include nylon, polyurethane, polycarbonate, polyacrylonitrile, polyethyleneoxide, polyaniline, polyvinyl carbazole, polystyrene and poly(vinyl phenol) [Schreuder-Gibson et al., J. Adv. Mater. 2002; 34: 44–55; Tsaia et al., J. Electrostatics 2002; 54: 333–41; Krishnappa et al., Mat Res Soc Symp Proc 2002, 702:U6.7.1–U 6.7.6; Wang et al., Nano Letters 2002; 2: 1273–5; Senador et al., Mat. Res. Soc. Symp. Proc. 2001; 661: KK5.9.1–KK 5.9; MacDiarmid et al., Synthetic Metals, 2001; 119:27–30; Bognitzki et al. Adv Master 2001; 13:70–2; Megelski et al., Macromolecules 2002; 35:8456–66; and Kenawy et al. Macromoleuclar Bioscience 2002; 2:261–6]. However, the projected applications for the nanofibers based on these polymers included protective clothings, developing liquid, gas/molecule filtration devices, nonosensors, conductive fibers, microelectronic wiring and interconnects as well as catalysts, not medical applications. These materials can be used to make nanofibers for medical applications.

Nanofibers of biodegradable polymers investigated for biomedical applications such as post surgical adhesion prevention membranes, as drug delivery systems, as scaffolds for tissue engineering, as haemostatic agents as well as wound dressings, were made of synthetic polymers such as the hydroxyacids like poly(lactic)/glycolic acid and their copolymers and poly(caprolactone) as well as natural polymers such as collagen and silk protein [Zong et al. Polymer 2002; 43:4403–12; Huang et al., J Biomater Sci Polym Edn. 2001b; 12:979–94; Buchko et al., Polymer 1999; 40:7397–407; Li et al., J Biomed Mater Res 2002; 60: 613–21; Yashimoto et al. Biomaterials 2003; 24: 2077–2082]. Other biodegradable polymers that could be used include polyanhydrides, polyhydroxyalkanoates, and polyurethanes, as well as natural polymer materials such as collagen, alginate, chitosan, and hyaluronic acid.

Polyphosphazenes are essentially linear polymers with alternating phosphorous and nitrogen atoms in their backbone with each phosphorous atom bearing two organic or organometallic side groups. The macromolecular intermediate poly(dichlorophosphazene) is obtained by the thermal ring opening polymerization of hexachlorocyclotriphosphazene (Scheme 1).

Scheme 1

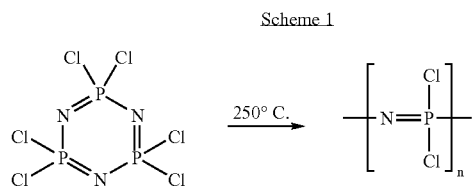

The polyphosphazenes are commonly synthesized by the nucleophilic substitution of chlorine atoms of polydichlorophoshazene by various nucleophiles (Scheme 2).

Scheme 2

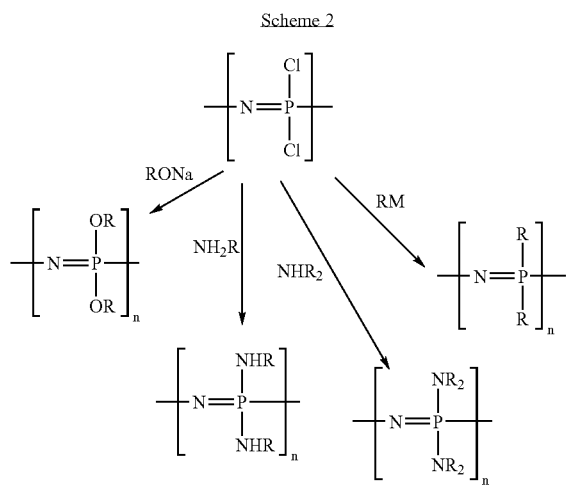

The polyphosphazenes, being an inorganic polymer, enjoys several advantages over organic polymers currently employed for various applications. These include superior properties such as high chain flexibility, high flame retardency and solubility in a variety of solvents. Due to the high chain flexibility of polyphosphazenes, the side groups on phosphorous atoms play a very significant role in determining the properties of the polymers [Allcock H R. Chem Eng News 1985; 63:22–36]. The polyphosphazene family consists so far of more than 700 different polymers each virtually unique with respect to the range of different properties that are accessible depending upon the nature of the side groups present. Polyphosphazenes having unusual thermal, optical, electrolytic conductivity, electroactivity, oxidative stability, biocompatibility and biodegradability have been synthesized by the incorporation of appropriate side groups.

Two of the stable polyphosphazenes synthesized initially were poly[bis(trifluoro ethoxy)phosphazene] and poly[bis (phenoxy)]phosphazene]. These are microcrystalline elastomers with high solvent resistance, high toughness as well as exhibit good biocompatibility. Further, mixed substituent fluoroalkoxy phosphazenes as well as those with different types of aryloxy groups such as those with p-methyl phenoxy, phenyl phenoxy or cosubstituting any of these groups with hydrophilic groups such as alkyl amino or methoxy polyethylene glycol side groups have been developed. These elastomers have been used in aerospace applications, military hardware, seals, gaskets, tubes, pipes, in nonflammable heat, sound and electrical insulation, highly efficient membranes for liquid or gas phase separations as well as for various biomedical applications.

Biodegradable polyphosphazenes can be synthesized by incorporating side groups such as imidazolyl, amino acid esters, glycosyl, glyceryl as well as lactic or glycolic acid esters. Further the degradation rate of these polymers can be further modulated by incorporating aryloxy side groups which are known to retard polyphosphazene backbone hydrolysis [Laurencin, J. Biomed. Mater. Res. 27, 963 (1993)]. Biodegradable polyphosphazenes have been extensively investigated for various biomedical applications and has been found to be a potential candidate for controlled drug delivery applications as well as scaffolds for tissue engineering [Laurencin, et al. J. Biomed. Mater. Res. 30, 1338 (1996); Ibim, et al., Biomaterials 18, 1565 (1997); Ambrosio, et al. Biomaterials 23, 1667 (2002)].

Polyphosphazenes are also known to form miscible blends with a variety of other polyphosphazenes or with various organic polymers [Ibim 1997; Ambrosio 2002]. Blending polyphosphazenes with other polymers provides another facile route to modulate the properties of the polymer. Blending biodegradable polyphosphazenes with other biodegradable polymers such as poly(lactic-co-glycolide) (PLAGA) has shown to modulate the degradation rate of the parent polymers and at the same time neutralize the acidic degradation products of PLAGA by the degradation products of polyphosphazenes. Further blends of polyphosphazenes with PLAGA has shown significant improvement in cell attachment ability compared to the parent polymers making them candidates as scaffolds for tissue engineering. Similarly composites of polyphosphazenes with hydroxyapatites have been developed as potential candidates for bone tissue engineering. This clearly shows that polyphosphazenes can find applications in almost all areas of current technology.

Blending of polyphosphazenes with other polyphosphazenes or with other organic polymers can result in an enticing variety of polymers with unique property profiles. The material properties, particularly the mechanical properties, of the nanofibers can be modified by incorporating nanosized particles or fillers to generate composite nanofibers. These can be structural or buffering materials, or drug particles.

Nanofibers can be formed of non-biodegradable or biodegradable polyphosphazenes, blends of polyphosphazenes with a biodegradable organic polymer (such as PLAGA), or composite nanofibers from polyphosphazene and nanocrystals of hydroxyapatite (HAP).

Medical Applications

The nanofibers can be formulated using standard technology to make woven or non-woven meshes, drug delivery devices, bandages, fabrics, matrices for tissue repair or regeneration, or other materials.

In the practice of surgery there currently exists a need for absorbable fibers and surgical meshes with improved performance. For example, there is currently a need for an absorbable monofilament fiber with a prolonged strength retention that can be used as a suture material. Such a product would potentially be useful in the treatment of patients with diabetes, obesity, nutritional impairment, compromised immune systems, or other conditions such as malignancy or infection that compromise wound healing.

There also exists a need for improved surgical meshes. For example, an absorbable hernia mesh with prolonged strength retention could have many advantages over the non-absorbable synthetic meshes currently used in hernia operations (Klinge et al. 2001). Long-term implantation of these non-absorbable meshes is not considered ideal because they can lead to complications such as adhesions (fistula formation), pain, and restriction of physical capabilities (Klinge et al., 2001). If implanted into surgical sites that are contaminated or have the potential to become contaminated, 50–90% of these non-absorbable implants will need to be removed (Dayton et al. 1986). These implants are also not ideal for use in pediatric patients where they could hinder growth (Klinge et al., 2001). To date, the use of absorbable synthetic surgical meshes in hernia repair has been found to almost invariably result in large incisional hernias that require revision operations because of the relatively short-term strength retention of these materials (Klinge et al., 2001). However, it is thought that an absorbable hernia mesh with prolonged strength retention could solve this problem providing a mechanically stable closure, reduce the incidence of adhesions and risks of infection, and be suitable for use in pediatric patients.

In addition to the need for improved meshes for hernia repair, there are also needs for improved meshes and patches for other procedures. In pericardial repair there exists a need for a surgical material that will prevent adhesions between the sternum and heart following open-heart surgery. There are also similar needs to prevent adhesions in spinal and gynecology procedures that could be addressed with improved surgical meshes and patches.

Animal and human derived patches are currently used fairly extensively in cosmetic surgery, cardiovascular surgery, general surgery (including hernia repair), and in urology and gynecology procedures for the treatment of conditions that include vaginal prolapse and urinary incontinence. There is however reported to be growing concern about the use of animal and human derived biomaterials because of the risks associated with disease transmission. Synthetic absorbable meshes and patches that may offer decreased risks of disease transmission are currently limited, can be inflammatory, and do not provide prolonged strength retention. Thus there currently exists a need to develop new absorbable meshes for these procedures as well. Ideally, these products should have prolonged strength retention, induce minimal inflammatory responses that resolve, provide mechanically stable reinforcement or closure, offer anti-adhesion properties (where necessary), minimize the risks of disease transmission, and after absorption leave a healthy natural tissue structure.

There is thus a need to develop absorbable fibers with prolonged strength retention that could be used as suturing materials, or in surgical meshes. The latter, offering longer-term mechanical stability, could also be used in other procedures such as pelvic floor reconstruction, urethral suspension (to prevent stress incontinence using the mesh as a sling), pericardial repair, cardiovascular patching, cardiac support (as a sock that fits over the heart to provide reinforcement), organ salvage, elevation of the small bowel during radiation of the colon in colorectal cancer patients, retentive devices for bone graft or cartilage, guided tissue regeneration, vascular grafting, dural substitution, nerve guide repair, as well as in procedures needing anti-adhesion membranes and tissue engineering scaffolds. Strong absorbable fibers could also find other uses, for example, in synthetic ligament and tendon devices or scaffolds.

Drug delivery devices can consist of fibers, meshes, structures within matrices of other materials, or any of a number of other forms, where the drug is encapsulated within the matrix/fiber. These can be used as the delivery devices, coated with barriers to release or coatings such as enteric coatings which allow passage through the stomach prior to release of the encapsulated drug.

The present invention will be further understood by reference to the following non-limiting examples. These demonstrate that nanofibers of polyphosphazenes can be prepared by electrospinning wherein submicron sized fibers are produced from an electrostatically driven jet of polymer solution. The diameter as well as the morphology of the resulting fibers can be efficiently tuned by varying process parameters such as viscosity of the solution and potential gradient. Materials with excellent properties are developed by combining the advantages of nanoscale fibers with the unusual property profile available with polyphosphazenes.

EXAMPLE 1

Manufacture of Non-Degradable Polyphosphazene Nanofibers

Electrospinning Apparatus:

The electrospinning setup used in this study consisted of a 20 mL glass syringe, blunt end needle of different gauge sizes, a ground electrode (copper plate covered with aluminum foil/interface fabric/Teflon coated sheet) placed at a predetermined distance from the needle tip. The syringe was fixed perpendicular to the collection screen and the polymer solution was allowed to flow under gravity. A Gamma High Voltage Supply ES40P -20W (0–40 kV, ES40P-20W; Gamma High Voltage Research, Florida) with a low current output was employed in the current study. A positive voltage was applied to the polymer solution in the glass syringe by attaching an alligator clip to the needle from the positive lead.

Different system parameters and processing variables affect the electrospinning process. The system parameters that could be modulated to optimize the fabrication method involve the molecular weight and molecular weight distribution of the polymer and solution properties such as the viscosity, conductivity as well as surface tension of the polymer solution. Further tuning of the spinning process can be achieved by varying process parameters such as electric potential, flow rate of the polymer solution, concentration of the polymer solution, the distance between the needle tip and collecting screen, diameter of the capillary orifice, temperature, air velocity and humidity of the chamber and by using static or rotating collection screen.

Nanofiber Fabrication from Non Degradable Polyphosphazenes:

Preparation of nanofibers of poly[bis(carboxylato phenoxy)phosphazene (PCPP)

PCPP Synthesis:

PCPP was synthesized via the macromolecular substitution route of poly(dichlorophosphazene) according to a reported procedure [Allcock H R, Kwon S. Macromolcules 1989: 22; 75–79]. Briefly, PCPP was prepared by the nucleophilic substitution of poly(dichlorophosphazene) with the sodium salt of propyl p-hydroxybenzoate followed by the hydrolysis of ester groups to carboxylic acid. The composition of the polymer was confirmed by $^{31}$P NMR, $^1$H NMR and $^{13}$C NMR and the molecular weight in terms of gel permeation chromatography (GPC).

Structure of PCPP

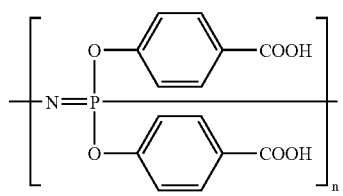

Fabrication of PCPP Nanofibers:

The electrospinning instrument used for the fabrication of the nanofibers was as discussed above. The spun fibers were collected on a collecting screen made of aluminium foil/synthetic fabric/Teflon sheet placed on a grounded copper plate. Different concentration of the polymer solutions were made in a solvent consisting of a mixture of dimethyl formamide (DMF) and tetrahydrofuran (THF) in the ratio of 4:1.

Different parameters were found to affect the morphology and diameter of the resultant nanofibers of PCPP. The morphology and the fiber diameter of the non-woven fiber meshes of PCPP were followed by scanning electron microscopy (SEM). For example, the effect of concentration of the polymer solution on electrospinning process was investigated using polymer concentration varying from 6–9% wt/volume of the polymer in DMF-THF mixture of ratio 4:1. The potential gradient used was 1.1 kV/cm and a blunt 18 gauge needle was used for spinning. SEM shows morphology and diameter of fibers formed at a polymer concentration of 6% by weight of the polymer. Random distribution of fibers occurred on the collection screen resulting in the formation of a non-woven mat. The SEM shows the presence of large number of beads along with nanofibers at this concentration. The average diameter of the fibers was found to be less than 150 nm.

At a concentration below 6% and in the absence of THF in the solvent mixture, electrospraying took place where the jet broke into droplets. Continuous fibers formed between concentration of 6–9% in DMF-THF mixture and above 9% the solution viscosity was very high making it difficult to spin. The viscosity corresponding to the concentration of 9% polymer weight was found to be 2753–2830 centipoise. SEM of the nanofibers obtained at a polymer concentration of 7% (wt/v) of the polymer in DMF-THF solvent mixture of ratio 4:1 with the potential gradient and needle size the same as discussed above, showed that the average thickness of the fibers were found to be less than 150 nm. The SEM showed the presence of beads, however the average number of beads per field was lower than that found at 6% solution concentration. The corresponding SEM obtained when PCPP was spun at a solution concentration of 8% by weight does not show significant differences in fiber diameter compared to concentration of 6 and 7%, however the number of beads found per field was lower than that at 7% by weight of polymer. SEM shows the morphology and diameter of PCPP nanofibers at a polymer concentration of 9% (weight by volume) of the polymer, with the formation of a uniform nanofiber mat with fewer beads at this concentration. The diameter of the PCPP fibers obtained was measured from the SEM micrographs and was found to be in the range of 66.67 nm±29 to 113±43 nm.

The voltage needed to eject the charged polymer jet from the needle tip depends mainly on the solution parameters. A comparison of the SEM of fibers obtained from 9% solution of PCPP when spun at a potential gradient 0.9 kV/cm at a magnification of ×10,000, the SEM of fibers spun at a potential gradient of 1 kV/cm at a magnification of 10,000×, the SEM when the fibers were spun at a potential gradient of 1.1 kV/cm, and the SEM of fibers spun at a potential gradient of 1.2 kV/cm, shows that the potential gradient of 1.2 kV/cm produced uniform fibers with the lowest diameters among the various potential gradient investigated for PCPP.

The morphology and diameter of the PCPP nanofibers when spun using a 9% weight by volume of polymer solution at a potential gradient of 1.2 kV/cm at various distance from the collection screen was studied. The SEM of fibers obtained when the distance between the needle tip and collection screen was kept at 20, 25, 30 and 33.33 cm demonstrated that a distance of 25–30 cm gives uniform fibers having smaller diameters compared to other distances studied. The optimized concentration of PCPP electrospinning was found to be at a polymer concentration of 9%, a potential gradient of 1.2 kV/cm and at a distance of 25 cm.

Preparation of nanofibers of poly[bis(p-methyl phenoxy)phosphazene (PNmPh)

PNmPh Synthesis:

PNmPh was synthesized via the macromolecular substitution route of poly(dichlorophosphazene) according to Allcock H R, Fitzpatrick R J. Chemistry of Materials, 1991:3; 1120–1132. Briefly, PNmPh was prepared by the nucleophilic substitution of poly(dichlorophosphazene) with the sodium salt of p-methyl phenol in an autoclave reactor at 160° C. for 24 h at 60 psi. The structure of the polymer was confirmed by $^{31}$P NMR, $^1$H NMR and $^{13}$C NMR and the molecular weight in terms of gel permeation chromatography (GPC). The number average molecular weight of the polymer used was 642,000 and weight average was 1,909,000 with a polydispersity of 3.0.

Structure of PNmPh

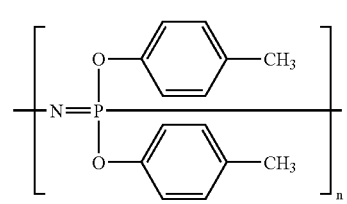

Fabrication of PNmPh Nanofibers:

The morphology and diameters of the nanofibers from PNmPh can be varied by varying parameters such as concentration/viscosity of the solution, molecular weigh the polymer, electric potential, distance between the needle tip and the collecting screen as well as the size of the needle. The polymer was dissolved in chloroform and the solution was used for the electrospinning process. The SEM of PNmPh fibers obtained by spinning a 6% solution of the polymer in chloroform at a potential gradient of 1 kV/cm using an 18 gauge needle showed that, as compared to PCPP, the number of beads formed in the case of PNmPh was very low. However the average size of the fibers was found to be higher compared to PCPP.

SEMs were made of fibers obtained at concentrations of 7, 8 and 9% by weight of the polymer. Concentrations of 8% yielded uniform fibers. The average diameters of the fibers were found to be in the range of 0.915±0.29 µm–1.423±0.43 µm. The morphology and diameter of the fibers at various potential gradients (0.9–1.2 kV/cm) was studied. The SEM of fibers spun at a concentration of 8% at a potential gradient of 1.1 kV/cm at a magnification of 5,000× and the SEM of fibers spun at a concentration of 8% at a potential gradient of 1.2 kV/cm at a magnification of 5,000× were compared and it was determined that as the potential gradient was increased, fibers with smoother surface morphology was obtained. As is evidenced from the SEMs, the potential gradient of 1.2 kV/cm gives uniform fibers with the smoothest surface morphology. The variation in morphology and diameters of the fibers when the distance of the needle tip from the collection screen was varied from 20–33.33 cm was also studied. The SEM of fibers spun when the distance between the collection screen and needle tip was kept at 25 cm and the corresponding SEM when the distance was 30 cm. As the distance increases, the fiber diameter increases. The optimized condition for PNmPh electrospinning was found to be of 8% (weight by volume) of the polymer in chloroform at a potential gradient of 1.2 kV/cm and at a distance of 25 cm.

EXAMPLE 2

Manufacture of Degradable Polyphosphazene Nanofibers

Preparation of nanofibers of poly[bis(ethyl alanato)phosphazene (PNEA)

PNEA Synthesis:

PNEA was synthesized via the macromolecular substitution route of poly(dichlorophosphazene) according to Allcock et al. AG, Biomaterials 1994:15; 563–569. Briefly, PNEA was prepared by the nucleophilic substitution of poly(dichlorophosphazene) with a large excess of ethyl alanate. The structure of the polymer was confirmed by $^{31}$P NMR, $^{1}$H NMR and $^{13}$C NMR and the molecular weight .in terms of gel permeation chromatography (GPC). The number average molecular weight of the polymer used was 236,000 and weight average was 437,000 with a polydispersity of 1.9.

Structure of PNEA

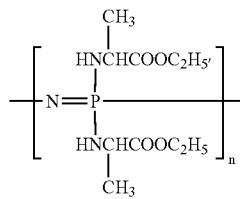

Fabrication of PNEA Nanofibers:

As discussed above, the morphology and diameters of the nanofibers from PNEA can also be varied by varying parameters such as concentration/viscosity of the solution, molecular weight the polymer, electric potential, distance between the needle tip and the collecting screen as well as the gauge size of the needle. In a typical example, the polymer solution in ethanol at a concentration of 27 wt % by volume was used for spinning. The SEM of PNEA fibers obtained by spinning at a potential gradient of 1.75 kV/cm and using an 18 gauge needle showed that the diameters of the fibers obtained under the present experimental condition were in the nanometer range.

Preparation of nanofibers of biodegradable copolymer poly (50% ethyl alanato) (50% methyl phenoxy)phosphazene] (PNEA-mPh)

PNEA-mPh Synthesis:

PNEA-mPh was synthesized via the sequential macromolecular substitution route of poly(dichlorophosphazene) according to a modified form of reported procedure. Briefly, PNEA-mPh was prepared by the nucleophilic substitution of 50% chlorine atoms of poly(dichlorophosphazene) with sodium salt of p-methyl phenol followed by the substitution of the rest of the chlorine atoms with ethyl alanato groups. The structure of the polymer was confirmed by $^{31}$P NMR, $^{1}$H NMR and $^{13}$C NMR and the molecular weight in terms of gel permeation chromatography (GPC). The number average molecular weight of the polymer used was 367,000 and weight average was 5,271,000 with a polydispersity of 14.4.

Structure of PNEA-mPh

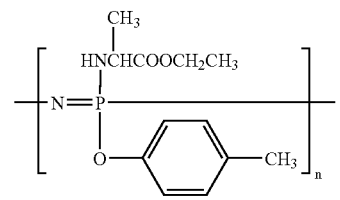

Fabrication of PNEA-mPh Nanofibers:

As discussed above, the morphology and diameters of the nanofibers from the copolymer PNEA-mPh can be varied by varying parameters such as concentration/viscosity of the solution, molecular weight the polymer, electric potential, distance between the needle tip and the collecting screen as well as the size of the needle. In a typical example, the polymer solution in THF at a concentration of 7% (weight by volume) was used for spinning. The SEM of PNEA-mPh fibers obtained by spinning at 20 KV at a distance of 30 cm using a 16 gauge needle. The fibers obtained under the present experimental conditions were found to have large number of beads on them however, the bead formation during spinning process can be almost eliminated by optimizing the parameters discussed before.

Preparation of Nanofibers of Blends of Polyphosphazene

Blends of Poly(lactide-co-glycolide) with Poly (50% Ethyl Alanato) (50% Methyl phenoxy)phosphazene] (PNEA-mPh):

Blend Fabrication:

Polyphosphazenes are known to form blends with other polyphoshpazenes as well as with a variety of non degradable and degradable polymers. Blends of polyphosphazenes with PLAGA can be prepared by mutual solvent approach as reported earlier. PLAGA with lactide-glycolide concentration of 85:15 was used for the present study. Blends (50:50) of PLAGA with PNEA-mPh were prepared by dissolving both the polymer in THF.

Fabrication of Blend Nanofibers from PLAGA and PNEA-mPh:

The morphology and diameters of the nanofibers of blends of polyphosphazenes with various polymers such as PLAGA can be varied by varying parameters such as concentration/viscosity of the solution, molecular weight of the polymer, electric potential, distance between the needle tip and the collecting screen as well as the gauge size of the needle. In a typical example, the polymer solution in THF at a concentration of 10% (wt by volume) by volume was used for spinning. The SEM of blend fibers of PLAGA and PNEA-mPh obtained by spinning at an electric potential of 33 kV and at a distance of 30 cm using an 18 gauge needle. The blend systems investigated was found to not form a completely miscible system. That may be the reason for the presence of fibers with large variations in size. However several biodegradable polyphosphazenes are known to form miscible blends with PLAGA and such system can give rise to more uniform fiber mat. The miscibility of such blend system in the nanofibers can be followed by transmission electron microscopy (TEM).

Preparation of Composite Nanofibers of Polyphosphazenes

Composite nanofibers of poly[bis(ethyl alanato)phosphazene](PNEA) and nanocrystals of HAP Composite Nanofiber Fabrication PNEA was synthesized via the macromolecular substitution route of poly(dichlorophosphazene) according to Allcock 1994. Briefly, PNEA was prepared by the nucleophilic substitution of poly(dichlorophosphazene) with a large excess of ethyl alanate. The structure of the polymer was confirmed by $^{31}$P NMR, $^1$H NMR and $^{13}$C NMR and the molecular weight .in terms of gel permeation chromatography (GPC). The number average molecular weight of the polymer used was 236,000 and weight average was 437,000 with a polydispersity of 1.9. Nanocrystals of HAP having a average particle size of about 20 nm (Berkeley Advanced Biomaterials Inc, USA) was used for the present study. The polymer was dissolved in ethanol solution (27% wt/v) and HAP (suspension in ethanol; 46.3%) was then dispersed in the polymer solution by sonication. The suspension was then used for the electrospinning process. The electrospinning was carried out at an electric potential of 33 kV and at a distance of 30 cm using an 18 gauge needle.

The SEM of composite nanofibers formed from PNEA and HAP nanocrystals showed that most of the HAP particles were found to be entrapped within the fibers and a small amount were found dispersed within the matrix. The presence of polymer beads in the present system as well as HAP particles can be reduced by varying the process and solution parameters of electrospinning as discussed before.

What is claimed is:

1. A device comprising biocompatible polymeric nanofibers having a diameter of between 100 and 1000 nm, wherein the device is selected from the group consisting of a medical device, sutures, drug delivery device, matrix or scaffold for tissue engineering, repair or regeneration device, medical prosthesis, or cosmetic skin mask, and wherein the polymer has the formula shown below:

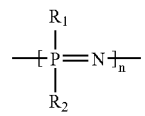

wherein R1 and R2 are independently selected from the group consisting of

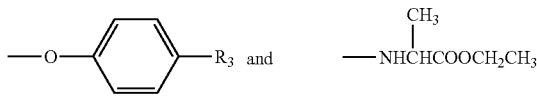

wherein R3 is CH$_3$ or COOH;

and n is an integer ranging from about 10 to about 500.

2. The device of claim 1, wherein the nanofibers further comprise a polymer selected from the group of nondegradable polymers consisting of nylon, polyurethane, polycarbonate, polyacrylonitrile, polyethyleneoxide, polyaniline, polyvinyl carbazole, polystyrene and poly(vinyl phenol) and the group of biodegradable polymers consisting of polyhydroxyacids, poly(caprolactone, polyanhydrides, polyhydroxyalkanoates, polyurethanes, collagen, alginate, chitosan, and hyaluronic acid, and blends and copolymers thereof.

3. The device of claim 1 wherein the nanofibers are formed of non-biodegradable or biodegradable polyphosphazenes, blends of polyphosphazenes with a biodegradable organic polymer, or composite nanofibers of polyphosphazene and nanocrystals or nanosized particles.

4. The device of claim 1, wherein the nanofibers further comprise particles selected from the group consisting of hydroxyapatite, structural materials, buffering materials, and drug particles.

5. The device of claim 1 wherin the nanofibers are formed from a polymer solution having a concentration of 6—9% in an organic solvent.

6. The device of claim 1 wherin the nanofibers form a wrap knitted mesh, woven mesh, or nonwoven mesh.

7. The device of claim 1, wherein the device is a suture.

8. The device of claim 1, wherein the device is a drug delivery device, further comprising a drug or biologically active agent.

9. The device of claim 1 wherein the medical device is selected from the group comprising general surgical mesh, hernia mesh, pericardial patch, anti-adhesion patch, cardiovascular patch, guided tissue regeneration patch, sling, monofilament suture, multifilament suture, braid, ligament, tendon, nerve guide, vascular graft, and dura.

10. The device of claim 1 wherein the nanofibers are monofilaments, multifilaments, or braided structures.

* * * * *

UNITED STATES PATENT AND TRADEMARK OFFICE
CERTIFICATE OF CORRECTION

PATENT NO. : 7,235,295 B2
APPLICATION NO. : 10/938493
DATED : June 26, 2007
INVENTOR(S) : Cato T. Laurencin et al.

It is certified that error appears in the above-identified patent and that said Letters Patent is hereby corrected as shown below:

Column 12, line 28, replace "poly(caprolactone" with --poly(caprolactone)--.

Signed and Sealed this

Eighteenth Day of March, 2008

JON W. DUDAS
*Director of the United States Patent and Trademark Office*